United States Patent
Robbins et al.

(10) Patent No.: US 6,248,788 B1
(45) Date of Patent: *Jun. 19, 2001

(54) THERAPEUTIC METHOD WITH CAPSAICIN AND CAPASICIN ANALOGS

(75) Inventors: Wendye R. Robbins, San Francisco, CA (US); Peter S. Staats, Towson; Marco Pappagallo, Baltimore, both of MD (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/746,207

(22) Filed: Nov. 6, 1996

Related U.S. Application Data

(60) Provisional application No. 60/006,385, filed on Nov. 8, 1996.

(51) Int. Cl.$^7$ ............................. A01N 37/18; A61K 31/16
(52) U.S. Cl. ........................ 514/627; 514/625; 514/629
(58) Field of Search .................... 514/627, 625, 514/629

(56) References Cited

U.S. PATENT DOCUMENTS

| | | | |
|---|---|---|---|
| 4,313,958 | 2/1982 | LaHann | 424/324 |
| 4,424,205 | 1/1984 | LaHann et al. | 424/72 |
| 4,532,139 | 7/1985 | Janusz et al. | 514/627 |
| 4,544,668 | 10/1985 | Janusz et al. | 514/563 |
| 4,544,669 | 10/1985 | LaHann et al. | 514/563 |
| 4,592,912 * | 6/1986 | Nickolaus | 424/195.1 |
| 4,812,446 * | 3/1989 | Brand | 514/165 |
| 4,898,887 * | 2/1990 | Janusz et al. | 514/617 |
| 4,971,800 | 11/1990 | Chess et al. | 424/449 |
| 4,997,853 | 3/1991 | Bernstein | 514/621 |
| 5,260,313 | 11/1993 | Frome | 514/552 |
| 5,290,816 | 3/1994 | Blumberg | 514/691 |
| 5,411,738 | 5/1995 | Hind | 424/445 |
| 5,431,914 | 7/1995 | Adekunle et al. | 424/401 |
| 5,589,180 | 12/1996 | Hind | 424/402 |
| 5,665,360 | 9/1997 | Mann | 424/195.1 |
| 5,665,378 | 9/1997 | Davis et al. | 424/448 |
| 5,709,869 | 1/1998 | Hind | 424/402 |
| 5,788,982 | 8/1998 | Nadoolman et al. | 424/440 |
| 5,854,291 | 12/1998 | Laughlin et al. | 514/626 |
| 5,856,361 | 1/1999 | Holt et al. | 514/627 |
| 5,869,533 | 2/1999 | Holt | 514/627 |
| 5,910,512 | 6/1999 | Conant | 524/617 |
| 5,962,532 | 10/1999 | Campbell et al. | 514/627 |

FOREIGN PATENT DOCUMENTS

| | | |
|---|---|---|
| 90/14083 | 11/1990 | (WO). |
| WO 90/14083 * | 11/1990 | (WO). |
| 91/08738 | 6/1991 | (WO). |
| 93/17695 | 9/1993 | (WO). |
| 96/40079 | 12/1996 | (WO). |
| 98/40070 | 9/1998 | (WO). |
| 99/37675 | 7/1999 | (WO). |
| 99/43322 | 9/1999 | (WO). |

OTHER PUBLICATIONS

Craft et al., "Treatment Parameters of Desensitization to Capsaicin," Life Sciences, 51, pp. 1767–1775, 1992.*
Scholten, E., abstract of DE 4,414,502 A1, Nov. 2, 1995.*
Altymyshev, A. A. et al., abstract to SU 1,794,454 A1, Feb 15, 1993.*
Geppetti et al., "Secretion, Pain and Sneezing Induced by the Application of Capsaicin to the Nasal Mucosa in Man," *Br. J. Pharmacol.*, 93, pp. 509–514 (1988).
Jancsó et al., "The Role of Sensory Nerve Endings in Neurogenic Inflammation Induced in Human Skin and dn in the Eye and Paw of the Rat," *B. Jr. Pharmac. Chemother.*, 32, pp. 32–14 (1968).
Watson et al., "Post–Herpetic Neuralgia and Tropical Capsaicin," *Pain*, 33, pp. 333–340 (1988).
Craft and Porreca, "Treatment Paraameters of Desensitization to Capsaicin," *Life Sciences*, 51, (1992), pp. 1767–1775.
McMahon et al., "The Consequences of Long–Term Topical Capsaicin Application in the Rat," *Pain*, 44 (1991), pp. 301–310.
Ton et al., *British Journal of Pharmacology*, 10 (1955), pp. 175–182.

* cited by examiner

Primary Examiner—Dwayne C. Jones

(57) ABSTRACT

Application of capsaicin (or a capsaicin analog) in a concentration from about 5% to about 10% by weight has been discovered to be an extremely effective therapy for treating neuropathic pain. In the practice of the present invention, a regional anesthetic, preferably by means of a somatic or neuraxial block, is administered to the affected area to minimize the expected side effects from them subsequent capsaicin application. Using the protocols described, patients with previously resistant neuropathic pain have experienced pain relief for periods of two to seven weeks.

17 Claims, No Drawings

THERAPEUTIC METHOD WITH CAPSAICIN AND CAPSICIN ANALOGS

CROSS-REFERENCE TO RELATED APPLICATION

This is an application based on provisional patent application Ser. No. 60/006,385, filed Nov. 8, 1996.

FIELD OF THE INVENTION

The present invention generally relates to peripheral neuropathy and more particularly to methods for treating neuropathic pain by use of capsaicin (and/or a capsaicin analog) in high concentration in conjunction with a previously administered anesthetic to the affected areas.

This application claims the benefit of U.S. Provisional Application No. 60/006,385, filed Nov. 8, 1995.

BACKGROUND OF THE INVENTION

Neuropathic pain is thought to occur because of a sensitization in the peripheral and central nervous systems after an initial injury to the peripheral system. Direct injury to the peripheral nerves as well as many systemic diseases including AIDS/HIV, Herpes Zoster, syphilis, diabetes, and various autoimmune diseases, can induce this disorder. Neuropathic pain is typically burning, shooting, and unrelenting in its intensity and can sometimes be more debilitating that the initial injury or the disease process which induced it. Unfortunately, the few remedies that have been reported to alleviate this condition is effective in only a small percentage of patients.

Capsaicin, a pungent substance derived from the plants of the Solanaceae family (hot chili peppers) has long been used as an experimental tool because of its selective action on the small diameter afferent nerve fibers, or C fibers, that are believed to mediate pain. From studies in animals, capsaicin appears to trigger C fiber membrane depolarization by opening cation selective channels for calcium and sodium. Although detailed mechanisms are not yet known, capsaicin mediated effects include: (i) activation of nociceptors in peripheral tissues; (ii) eventual desensitization of peripheral nociceptors to one or more stimulus modalities; (iii) cellular degeneration of sensitive unmyelinated C fiber afferents; (iv) activation of neuronal proteases; (v) blockage of axonal transport; and (vi) the decrease of the absolute number of C fibers without affecting the number of myelinated fibers.

Because of capsaicin's ability to desensitize nociceptors in peripheral tissues, its potential analgesic effects have been assessed in various clinical trials. However, since the capsaicin application itself frequently causes burning pain and hyperalgesia apart from the neuropathic pain being treated, patient compliance has been poor and the drop out rates during clinical trials have exceed fifty percent. The spontaneous burning pain and heat hyperalgesia are believed to be due to intense activation and temporary sensitization of the peripheral nociceptors at the site of capsaicin application (primary hyperalgesia). Mechanical hyperalgesia evident in areas surrounding the site of topical application appears to originate from central sensitization of dorsal horn neurons involved in pain transmission (secondary hyperalgesia). Because of these side effects, the maximal capsaicin concentration used in previous human studies has been limited to 0.075%.

Analogs of capsaicin with similar physiological properties are known. For example, resiniferatoxin is described as a capsaicin analog by inventor Blumberg, U.S. Pat. No. 5,290,816, issued Mar. 1, 1994. Inventor Brand in U.S. Pat. No. 4,812,446, issued Mar. 14, 1989, describes capsaicin analogs and methods for their preparation. Further, inventors LaHann et al. in U.S. Pat. No. 4,424,205, issued Jan. 3, 1984, cite Newman, "Natural and Synthetic Pepper-Flavored Substances" published in 1954 as listing pungency of capsaicin-like analogs. Ton et al., *British Journal of Pharmacology*, 10, pp. 175–182 (1955) discuss pharmacological actions of capsaicin and its analogs.

SUMMARY OF THE INVENTION

One aspect of the present invention comprises administering an anesthetic to a patient suffering neuropathic pain followed by applying a composition including from about 5% to about 10% of capsaicin (and/or a capsaicin analog) by weight to the patient. The capsaicin (and/or capsaicin analog) containing composition preferably is administered topically, is applied more than once, and includes a vehicle with skin penetrating properties. The anesthetic preferably is by means of a somatic or neuraxial block administered prior to application of the capsaicin (and/or capsaicin analog) composition, which can be of any local anesthetic, and can be administered such as by injection in the epidural space adjacent to the spine. The prior administration of a proximal neural block sufficiently desensitizes C fibers to the expected side effects of the subsequent capsaicin application. The administration of the anesthetic along with the subsequent administration of capsaicin appears to alleviate the symptoms of peripheral neuropathy for a prolonged period of time. For example, patients with previously resistant neuropathic pain have experienced pain relief for periods of two weeks to seven weeks following the high dose capsaicin treatment as described in this invention.

DETAILED DESCRIPTION OF THE PREFERRED EMBODIMENTS

Practice of the invention prevents the burning pain and hyperalgesia to both heat and touch typically occurring after even the relatively low concentration applications of capsaicin ointment known to the art. Such burning pain is avoided by first administering an anesthetic, such as a block (somatic or neuraxial), so as to cause regional anesthesia in the areas to be treated.

It is believed feasible to employ topically active anesthetic cremes in addition to or in lieu of the anesthetic block to prevent the side effects from the application of the high dose capsaicin, thus reducing or obviating the need to perform a somatic block.

A wide variety of suitable anesthetics for the block are known and useful, such as tetracaine hydrochloride and the like. Due to its short action, 2-chloroprocaine hydrochloride is preferred among the suitable local anesthetics. The local anesthetic is administered at an appropriate site, one preference being at the epidural space adjacent the spine for neuropathic pain originating below a patient's waist (such as in a patient's legs or feet).

When the anesthetic administered has taken effect in providing analgesia, then a composition including capsaicin (and/or a capsaicin analog) is administered, preferably by topical application, at least once. This composition preferably is formulated with a vehicle having a skin penetrating and skin absorbing agent. One suitable such vehicle is commercially available as EUCERIN cosmetic skin lotion (Beiersdorf Aktiengesellschaft). The topical application of the capsaicin (and/or capsaicin analog) containing composition delivers the drug through the skin. Because skin is a structurally complex, relatively thick membrane, molecules moving from the environment into and through intact skin must first penetrate the stratum corneum and any material on its surface, then penetrate the viable epidermis, the papillary dermis, and the capillary walls. To be so absorbed, molecules must overcome a different resistance to penetration in the different types of tissue. It is for these reasons that the formulation is prepared so as to increase skin permeability and to increase the permeability in particular of the stratum corneum. Such skin penetrating and absorbing agents are known to the art. For example, the capsaicin composition can include one or more penetration-enhancing agents such as those described by U.S. Pat. No. 4,971,800, issued Nov. 20, 1990, inventors Chess et al.

At present, capsaicin is commercially available in over-the-counter topical preparations at concentrations of 0.025% and 0.075%. However, capsaicin concentrations in the range of 5–10% appear to be necessary to sufficiently desensitize the C fiber population to effectuate prolonged relief from many of the symptoms of peripheral neuropathy. Thus, capsaicin compositions necessary for the practice of this invention must be prepared by mixing pure capsaicin powder to the desired concentration by weight, from about 5% to 10%, more preferably at about 7.5%, in the selected vehicle. Such an admixture of high concentration of capsaicin is a substance that must be handled with care and preferably is prepared by a skilled technician or a trained pharmacist. Where a capsaicin analog is selected to replace some or all of the capsaicin, then the analog can be selected from those analogs with similar physiological properties to capsaicin as are known to the art.

The expected side effects of the high dose application of the capsaicin composition are believed to be from intense C fiber discharge occurring during the excitatory phase before C fiber desensitization. However, the prior administration of an anesthetic, such as a nerve block, proximal to the site of application in accordance with the invention eliminates or substantially abates such side effects. If some "breakthrough pain" occurs despite the anesthetic, then this pain may be treated by administering an analgesic such as a narcotic analgesic (e.g., the various alkaloids of opium, such as morphine, morphine salts, and morphine analogs such as normorphine and so forth).

It is important to note that somatic and neural blocks have been given to patients with peripheral neuropathy in an effort to relieve their pain. However, patients did not experience pain relief beyond the expected duration of the anesthetic. Because the patients in the following Examples describe long term pain relief much beyond the expected duration of the regional anesthetic, this relief cannot be due to the action of the anesthetic alone and is due to the combination of the block and capsaicin (since administration of the high concentration capsaicin without the anesthetic would not be possible). As will be described, application of high dose capsaicin combined with a prior administration of a regional anesthetic appear to be an extremely effective therapy for treating resistant neuropathic pain.

EXAMPLE 1

The following protocol employing 7.5% capsaicin creme with neuraxial or peripheral nerve blocks is more fully described to illustrate in (but not to limit) the practice of this invention. This protocol was used to treat the patients described in Examples 2–4. Capsaicin powder is mixed to a total concentration of 7.5% in EUCERIN creme. An 18 g i.v. is placed in the patient's upper extremity vein. Regional anesthesia is then administered either by lumbar epidural catheter or blockade of the major peripheral nerves of the affected area. Approximately 15 cc of the capsaicin creme is applied to the affected area and then is covered with an occlusive dressing. After thirty minutes, the creme is wiped off and the affected area is then washed with warm water and soap. After an additional thirty minutes, the capsaicin cream is reapplied then removed as described. If breakthrough burning occurs as a result of the capsaicin application, intravenous opiates are given to alleviate this discomfort.

EXAMPLE 2

The patient was a 56 year old Hispanic male who had undergone a bunionectomy eight years ago. Persistent pain developed in the region of the scar and over all of the digits. In an effort to relieve his severe pain, podiatric surgical resection of his third toe and metatarsal was performed approximately fourteen months prior to the capsaicin treatment. Despite the second surgery, his pain gradually increased in intensity and distribution, and covered the entire plantar and ventral surfaces of his foot.

The patient rated the burning at 10/10 on the visual analog scale. Additionally, he reported cooling hyperalgesia, scaling, drying, and general coolness of the skin on that extremity. He was unable to distinguish the temperature of shower water falling on his foot. He became unable to wear a shoe on the foot, became chair and bed bound, and was able to ambulate only with a cane. Previous treatments included somatic nerve blocks at the ankle (which only intensified the pain as the anesthetics wore off), physical therapy (which he was unable to tolerate), and propoxyphene with acetaminophen (which provided minimal relief of pain).

On examination, he was cachectic. His right foot was exquisitely tender and erythematous. The skin over the extremity was cool, dry and scaly. He was hyperesthetic to light touch.

Following the protocol, an 18 g i.v. was placed in his left wrist. An epidural catheter was placed at the L2-3 interspace and dosed with 12 cc of 0.5% Marcaine. A surgical block was documented from T10-S2, and then 7.5% capsaicin creme was applied and then reapplied to the plantar and dorsal surfaces of his foot.

At twenty-four hours post procedure, the patient reported that his previous pain had disappeared except for over a small part on the plantar aspect of the foot under the second toe. He was able to wear a shoe on the foot, and began ambulating on a regular basis.

Five weeks post procedure, the patient reported absence of pain except for under the second toe. On examination, the foot was non-tender and warm, with intact, moist skin. He could distinguish light touch, and pinprick, and reported that these sensations felt identical to examination of the opposite foot. He was able to distinguish heat from cold. Cooling hyperalgesia was absent.

The patient returned to the clinic, and underwent reapplication of capsaicin creme under the same protocol. He again experienced post procedure burning for one week which was treated with short acting opiates. At one week post reapplication, the patient reported complete relief of his previous burning pain except in the same small skip area. Complete relief except for the skip area was still reported at eight and one-half weeks post procedure.

EXAMPLE 3

The patient was an 80 year old black female who complained of severe sharp pains on the medial aspect of her left foot. After a bunionectomy six months previously, the patient developed an infection at the surgical site and subsequently developed osteomyelitis. She underwent amputation of the foot proximal to the first MTP joint. The patient had been unsuccessfully treated with posterior tibial nerve blocks, and short-acting opiates.

At the initiation of the capsaicin protocol, the patient complained of a burning pain over the medial aspect of her left foot rated 5/10 on the visual analog scale, difficulty with ambulation, and insomnia. On examination, a well healed amputation scar and sensory deficits to sharp touch and cold over the medial aspect of the foot was noted. A low dose regimen of nortriptyline and gabapentin was without significant benefit.

Following the protocol, an 18 g i.v. was placed in the patient's right wrist. Five cc's of 0.25% Marcaine was injected into the superficial peroneal, deep peroneal, saphenous, posterior tibial and sural nerves before 7.5% capsaicin was applied to the foot. Post procedure burning was successfully treated with short-acting opiates.

At five days post procedure, the patient reported that the previous pain had disappeared, except for a slight burning. At two weeks post procedure, the pain was rated 1/10 on the visual analog scale. The patient was intact to heat, cold, light, and sharp touch.

EXAMPLE 4

The patient was a 58 year old white female who presented complaints of right foot pain. Six months prior to the capsaicin protocol, the patient had developed thrombosis of the right femoral artery following placement of a femoral arterial catheter. An endarterectomy was performed and immediately thereafter, the patient developed a burning pain in the right foot. She reported that the foot had blanched, then became erythematous. Before the initiation of the capsaicin treatment, the patient reported swelling, stiffness, cooling hyperalgesia, allodynia, and a pain rated 10/10 on the visual analog scale. She was unable to bear weight on the affected foot.

The affected foot exhibited contractures, extreme tenderness to palpation, moderate to severe edema from the ankle to the toes, erythema, and coolness. Short-acting opiates had provided only modest relief and nortriptyline provided no relief.

Following protocol, an 18 g i.v. was placed in the left wrist. An epidural catheter was placed at the L3-4 interspace, and dosed with 15 cc of 2% Nesicaine. A surgical block was documented from T12-S2. Capsaicin was then applied and reapplied. On completion of the procedure, the patient reported intense burning which was adequately treated with a small dose of short-acting opiates.

At two weeks post procedure, the patient reported that her previous pain had significantly abated. She rated her current discomfort at 4/10. The patient began ambulating without crutches, and exercising the limb. On subsequent examination, the foot was warm, pink but not erythematous, and mild edema was present. The affected foot was non-tender to palpation and was now able to weight bear (with modest difficulty). The patient was intact to all sensation.

At three weeks post procedure, the patient reported continued resolution of edema and a pain rating of 4/10 on the visual analog scale.

All publications referred to in the above discussion are incorporated herein. It is to be understood that while the invention has been described above in conjunction with preferred specific embodiments, the description and examples are intended to illustrate and not limit the scope of the invention.

It is claimed:

1. A method for treating neuropathic pain of a human patient, said method comprising:

administering an afferent nerve fiber blocking regional anesthetic to the affected area; and administering a composition comprising capsaicin or a capsaicin analog, the capsaicin or capsaicin analog being present in a total concentration from about 5% by weight to about 10% by weight, wherein said composition is therapeutically effective in treating neuropathic pain in the affected area, and further wherein no more than two administrations are sufficient to afford significant relief of said neuropathic pain for at least two weeks.

2. The method as in claim 1 wherein said capsaicin or capsaicin analogue is capsaicin and the anesthetic is administered as a somatic block.

3. The method as in claim 1 wherein said capsaicin or capsaicin analog is a capsaicin analog.

4. The method as in claim 1 wherein the composition comprises both capsaicin and one or more capsaicin analogs.

5. The method as in claim 1 wherein the composition is administered topically.

6. The method as in claim 5 wherein the composition also includes an agent having skin absorbing properties.

7. The method as in claim 5 wherein the composition also includes an agent having skin penetrating properties.

8. The method as in claim 5, wherein said capsaicin or capsaicin analog is capsaicin.

9. The method as in claim 8, wherein said capsaicin or capsaicin analog is at a concentration of about 7.5% by weight or greater.

10. The method as in claim 5, wherein said capsaicin or capsaicin analog is a capsaicin analog.

11. The method as in claim 1 wherein the anesthetic is administered as a somatic block.

12. The method as in claim 1 wherein the anesthetic is administered as an epidural.

13. The method as in claim 1 further comprising the step of administering a narcotic analgesic.

14. The method as in claim 1 wherein the total concentration of the capsaicin or capsaicin analog is about 7.5% by weight or greater.

15. The method as in claim 1 wherein the composition comprises capsaicin and the anesthetic is administered as a neuroaxial block.

16. The method as in claim 1 wherein the composition comprises capsaicin and the anesthetic is administered as an epidural.

17. The method as in claim 1 wherein the anesthetic is administered as a neuroaxial block.

* * * * *